United States Patent [19]

Curro et al.

[11] Patent Number: 4,629,643
[45] Date of Patent: Dec. 16, 1986

[54] MICROAPERTURED POLYMERIC WEB EXHIBITING SOFT AND SILKY TACTILE IMPRESSION

[75] Inventors: John J. Curro; E. Kelly Linman, both of Cincinnati, Ohio

[73] Assignee: The Procter & Gamble Company, Cincinnati, Ohio

[21] Appl. No.: 740,125

[22] Filed: May 31, 1985

[51] Int. Cl.$^4$ .......................... B32B 3/24; B32B 3/26
[52] U.S. Cl. ..................... 428/131; 428/141; 428/156; 428/179; 604/385 R
[58] Field of Search ............... 428/131, 156, 141, 179; 128/156; 604/385 R

[56] References Cited

U.S. PATENT DOCUMENTS

| | | | |
|---|---|---|---|
| D. 278,468 | 4/1985 | Trotman et al. | D92/1.1 |
| 3,426,754 | 2/1969 | Bierenbaum et al. | 128/156 |
| 3,881,489 | 5/1975 | Hartwell | 128/287 |
| 3,886,941 | 6/1975 | Duane et al. | 604/385 |
| 3,911,187 | 10/1975 | Raley | 428/180 |
| 3,929,135 | 12/1975 | Thompson | 128/287 |
| 3,957,414 | 5/1976 | Bussey, Jr. et al. | 425/384 |
| 3,965,906 | 6/1976 | Karami | 128/287 |
| 3,966,383 | 6/1976 | Bussey, Jr. et al. | 425/388 |
| 3,979,494 | 9/1976 | Ericson | 264/154 |
| 3,987,792 | 10/1976 | Hernandez et al. | 128/284 |
| 3,989,867 | 11/1976 | Sisson | 428/132 |
| 3,994,299 | 11/1976 | Karami | 128/287 |
| 4,041,951 | 8/1977 | Sanford | 128/287 |
| 4,151,240 | 4/1979 | Lucas et al. | 264/504 |
| 4,155,693 | 5/1979 | Raley | 425/363 |
| 4,157,237 | 6/1979 | Raley | 425/363 |
| 4,200,103 | 4/1980 | Black et al. | 128/290 |
| 4,226,828 | 10/1980 | Hall | 264/555 |
| 4,248,822 | 2/1981 | Schmidt | 264/154 |
| 4,321,924 | 3/1982 | Ahr | 128/287 |
| 4,323,069 | 4/1982 | Ahr et al. | 128/287 |
| 4,327,730 | 5/1982 | Sorensen | 128/287 |
| 4,341,216 | 7/1982 | Obenour | 128/287 |
| 4,341,217 | 7/1982 | Ferguson et al. | 128/290 |
| 4,342,314 | 8/1982 | Radel et al. | 128/287 |
| 4,343,848 | 8/1982 | Leonard, Jr. | 428/156 |
| 4,351,784 | 9/1982 | Thomas et al. | 264/22 |
| 4,395,215 | 7/1983 | Bishop | 425/290 |
| 4,397,644 | 8/1983 | Matthews et al. | 604/378 |
| 4,463,045 | 7/1984 | Ahr et al. | 428/131 |
| 4,477,502 | 10/1984 | O'Sullivan | 428/35 |
| 4,508,256 | 4/1985 | Radel et al. | 228/152 |
| 4,509,908 | 4/1985 | Mullane, Jr. | 425/290 |
| 4,518,643 | 5/1985 | Francis | 428/131 |
| 4,552,709 | 11/1985 | Koger et al. | 264/504 |
| 4,572,360 | 2/1986 | Lischka, geg. Woitzik | 206/0.5 |
| 4,578,069 | 3/1986 | Whitehead et al. | 604/370 |

FOREIGN PATENT DOCUMENTS

| | | |
|---|---|---|
| 845826 | 8/1960 | United Kingdom . |
| 1160625 | 8/1969 | United Kingdom . |
| 2103933 | 3/1983 | United Kingdom . |

OTHER PUBLICATIONS

Commonly assigned, concurrently filed, co-pending U.S. patent application Ser. No. 740,112 filed on 5/31/85 in the name of Hugh A. Thompson.
Commonly assigned, concurrently filed, co-pending U.S. patent application Ser. No. 740,084 filed on 5/31/85 in the names of E. Kelly Linman, John J. Curro, and E. Weinshenker.
Commonly assigned, co-pending U.S. patent application Ser. No. 580,911 filed on 2/16/84 in the names of John J. Curro, Alan J. Trusty and George M. Vernon.

*Primary Examiner*—Paul J. Thibodeau
*Attorney, Agent, or Firm*—E. Kelly Linman; John V. Gorman; Richard C. Witte

[57] ABSTRACT

A microapertured polymeric web exhibiting a substantially uniform soft and silky tactile impression on at least one of its surfaces. In a preferred embodiment the present invention relates to webs exhibiting a fine scale pattern of discrete surface aberrations, each of said surface aberrations having its amplitude oriented substantially perpendicular to the surface in which said surface aberration originates. At least one tiny aperture (microaperture) is provided substantially coincidental with the maximum amplitude of each surface aberration. The discontinuity created by the aperture at the peak of each of the surface aberrations substantially reduces the resistance to both compression and shear of each individual surface aberration. In addition the volcroaperture are typically in the form of thin, irregularly shaped petals which not only reduce the total contact area with the user's skin, but which are also easily deflected when relative movement with the user's skin occurs. Microapertured webs of the present invention are also relatively quiet when subjected to movement, making them particularly suitable for use as topsheets and/or backsheets in disposable absorbent structures such as adult incontinent briefs.

8 Claims, 11 Drawing Figures

MICROAPERTURED POLYMERIC WEB EXHIBITING SOFT AND SILKY TACTILE IMPRESSION

TECHNICAL FIELD

The present invention has relation to a microapertured polymeric web exhibiting a substantially uniform soft and silky tactile impression on at least one of its surfaces.

The present invention has further relation to such webs exhibiting a fine scale pattern of discrete surface aberrations, each of said surface abberations having its amplitude oriented substantially perpendicular to the surface in which said surface aberration originates. A tiny operature (microaperture) is provided substantially coincidental with the maximum amplitude of each surface aberration. The discontinuity created by the aperture at the peak of each of the surface aberrations substantially reduces the resistance to both compression and shear of each individual surface aberration. In addition the volcano-like edges formed at the periphery of each microaperture are typically in the form of thin, irregularly shaped petals which not only reduce the total contact area with the user's skin, but which are also easily deflected when relative movement with the user's skin occurs. Thus microapertured webs of the present invention exhibit a significantly improved tactile response. In particular, the tactile response experienced when the user's skin contacts the volcano-like edges existing at the peak of each apertured surface aberration is a much softer sensation than that experienced with similar fine scale patterns of surface aberrations which are entirely unapertured. This difference in tactile impression is most pronounced in shearing actions, i.e., when the web's contact with the skin involves lateral movement relative to the skin rather than simple compressive movement perpendicular to the skin.

The present invention has further relation to such microapertured polymeric webs which are quiet when subjected to movement, i.e., they do not exhibit an embarrassing rustling noise when the wearer moves about.

The present invention, in a preferred embodiment, has further relation to such webs wherein each of said microapertured surface aberrations is free of planar areas which are large enough to inscribe a 4 mil diameter circle and is so spaced relative to all adjacent surface aberrations that the maximum diameter of any circle which can be inscribed in any planar surface intermediate said surface aberration and said adjacent surface aberrations on any portion of the web's surface is less than about 4 mils.

The present invention, in a particularly preferred embodiment, has further relation to substantially non-glossy microapertured polymeric webs wherein the surfaces intermediate the discrete microapertured surface aberrations are three-dimensionally curvilinear and correspond to the knuckles of a woven wire support structure, while the microapertured surface aberrations correspond to the interstices formed between the intersecting filaments comprising the woven wire support structure. The lack of significant planar areas helps to ensure that much of the light incident upon any portion of the web is diffusely reflected into a multiplicity of directions. Additionally the microapertures allow a portion of the incident light to be transmitted through the web and essentially eliminated. These two factors cause the microapertured web's surface to appear substantially non-glossy.

BACKGROUND ART

It has long been known in the disposable absorbent bandage art that it is extremely desirable to construct absorptive devices, such as disposable diapers, sanitary napkins, incontinent devices, absorbent wound dressings, and the like, presenting a dry cloth-like surface feel to the user's skin at any anticipated points of contact, e.g., as topsheets and/or backsheets.

While woven and non-woven fibrous webs are often employed for this purpose because of their pleasant surface feel, polymeric webs have been shown to exhibit more desirable fluid transport and fluid restraining characteristics in many circumstances.

It is, of course, known in the art to employ polymeric webs as both fluid pervious topsheets and fluid impervious backsheets on bandage structures. For example, U.S. Pat. No. 3,911,187 issued to Raley on Oct. 7, 1975 discloses a fluid impervious thermosplastic film suitable for use as a backsheet in structures such as disposable absorbent bandages, said film having a permanently embossed design which allegedly simulates woven fabric or cloth and which has edge curl resistance under machine stress. The embossed design is made up of latitudinally and longitudinally alternating hollow protuberances and depressions on both sides of the film. The width of the protuberances at their base vary from 5 mils to about 50 mils, most preferably from about 5 mils to about 20 mils. In the disclosed embodiment, the protuberances are comprised of a multiplicity of planar wall segments.

U.S. Pat. No. 4,343,848 issued to Leonard, Jr. on Aug. 10, 1982 discloses another fluid impervious embossed thermoplastic film suitable for use as a backsheet, said film being characterized in that one surface thereof is provided with a plurality of rows of protuberances having the shape of pyramids with square bases which extend perpendicular to both the longitudinal and the transverse axes of the film. The protuberances are joined at the edge of the bases by flat valley portions which intersect each other at right angles. It is alleged that the embossed film has a low coefficient of friction and increased embossed thickness. The protuberances in the disclosed embodiment preferably have a base from 4 mils to about 10 mils and a height from about ½ mil to about 4 mils. In the disclosed embodiment, the pyramids are comprised of substantially planar wall segments.

The use of fluid pervious polymeric webs as topsheets is also well known in the art. For example, U.S. Pat. No. 3,814,101 issued to Kozak on June 4, 1974, suggests the use of a fluid pervious hydrophobic film provided with a plurality of valvular slits which restrict the reverse flow of liquid from the absorbent element of the device as a topsheet for a disposable absorbent bandage.

For the purpose of interpreting the present specification and claims, the term "macroscopically expanded", when used to describe three-dimensional plastic webs, ribbons and films of the present invention, refers to webs, ribbons and films which have been caused to conform to the surface of a three-dimensional forming structure so that both surfaces thereof exhibit a three-dimensional pattern of surface aberrations corresponding to the macroscopic cross-section of said forming structure, the surface aberrations comprising said pattern being individually discernible to the normal naked eye, i.e., a normal eye having 20/20 vision unaided by any instrument that changes the apparent size or distance of an object or otherwise alters the visual powers of the eye, when the perpendicular distance between the viewer's eye and the plane of the web is about 12 inches. Such macroscopically expanded webs, ribbons and films are typically caused to conform to the surface of said forming structure by embossing, i.e., when the forming structure exhibits a pattern comprised primarily of male projections, by debossing, i.e., when the forming structure exhibits a pattern comprised primarily of female capillary networks, or by extrusion of a resinous melt directly onto the surface of a forming structure of either type. Also for the purpose of interpreting the present specification and claims, the term "planar", when utilized herein to describe plastic webs, ribbons and films of the present invention, refers to the overall condition of the web, ribbon or film when viewed by the normal naked eye on a macroscopic scale. In this context "planar" webs, ribbons and films may include webs, ribbons and films having a fine scale, yet visible, pattern of surface aberrations on one or both sides thereof, the surface aberrations comprising said visible pattern not being individually discernible to the normal naked eye when the perpendicular distance between the viewer's eye and the plane of the web is about 12 inches.

U.S. Pat. No. 3,929,135 issued to Thompson on Dec. 30, 1975, discloses one exemplary prior art fluid pervious, macroscopically expanded three-dimensional topsheet comprised of liquid impermeable material, but provided with tapered capillaries, said capillaries having a base opening in the plane of the topsheet and an apex opening remote from the plane of the topsheet, said apex opening being in intimate contact with the absorbent pad utilized in the disposable absorbent bandage.

Macroscopically expanded polymeric webs employing features to reduce gloss and improve tactile impression are also disclosed in the prior art, as is the use of such webs as topsheets and/or backsheets in disposable absorbent bandages. For example, commonly assigned U.S. Pat. No. 4,327,730 issued to Sorensen on May 4, 1982 discloses a disposable diaper having a fluid pervious textured topsheet of thermoplastic material. The topsheet is macroscopically expanded and is provided with a multiplicity of nubbles across its surface. The nubbles do not substantially alter the macroscopic profile of the film, but do impart a more cloth-like tactile impression and reduced gloss to the film.

An improved macroscopically expanded three-dimensional polymeric web exhibiting a substantially non-glossy visible surface and cloth-like tactile impression is disclosed in commonly assigned U.S. Pat. No. 4,463,045 issued to Ahr et al. on July 31, 1984. If desired, the macroscopically expanded three-dimensional polymeric web of Ahr et al. may be used as as fluid pervious topsheet in a disposable absorbent bandage. The visible surface of the macroscopically expanded three-dimensional polymeric web of Ahr et al. is preferably provided with a regularly spaced, microscopic pattern of surface aberrations, said pattern being too fine to be discernible by the normal naked eye when the perpendicular distance between the viewer's eye and the plane of the web is about 12 inches, but which pattern of surface aberrations is highly effective in substantially eliminating specular reflection of incident light. Said webs may be produced by means of a one sided forming process wherein said surface aberrations are transmitted through the thickness of the web during processing or by means of a two sided forming process wherein said surface aberrations are imposed directly onto the visible surface of the web. The surface aberrations may comprise either protuberances projecting generally outwardly from the surface of the web or depressions projecting generally inwardly from the surface of the web, e.g., the knuckle pattern of a fine woven wire embossing member. Macroscopically expanded three-dimensional polymeric webs of the type disclosed in the patent to Ahr et al. are often employed as alternatives for cloth and fiber structures which contact the wearer's skin.

The patent to Ahr et al. teaches the criteria which must be met with respect to the regularly spaced pattern of surface aberrations in order to diffusely reflect incident light and thereby eliminate gloss. It further teaches that in those situations where a more cloth-ike or fiber-like tactile impression in the resultant macroscopically expanded three-dimensional plastic web is also desired, the surface aberrations in the web should preferably exhibit an average amplitude of at least about 0.2 mils (i.e., 0.0002 inches), and most preferably at least about 0.3 mils (i.e., 0.0003 inches). According to Ahr et al., a more cloth-like or fiber-like tactile impression is percieved in macroscopically expanded three-dimensional plastic webs which meet the aforementioned amplitude criteria whether the surface aberrations comprise protuberances or depressions due to the fact that in either case the surface of the web is divided into at least two distinct planes separated from one another by a distance of at least 0.2 mils (i.e., 0.0002 inches). In the case of protuberances, it is the tops of the aberrations which contact the observer's skin, while in the case of depressions it is the substantially planar surface in which said aberrations originate which contacts the observer's skin. Ahr et al. further suggests that because said division is carried out in a fine microscopic pattern, only the reduced area of contact with the uppermost surface of the web and not existence of the pattern is tactually perceived.

Because of the superior fluid and vapor handling characteristics which can be provided in polymeric webs of the aforementioned type and their inherent cost advantages when contrasted to woven and non-woven fibrous webs, considerable effort has been expended to improve the consumer's reaction to the use of polymeric webs in contact with the skin. While much progress has been demonstrated in eliminating the negative consumer reaction to placing polymeric webs comprised of plastic in contact with the user's skin, particularly with respect to webs following the teachings of the aforementioned Ahr et al. patent, the approach generally taken has been to macroscopically expand the webs using three-dimensional patterns which make the web look more like a fibrous or cloth structure. Examples of this technique are the webs disclosed in commonly assigned U.S. Pat. No. 4,342,314 issued to Radel and Thompson on Aug. 3, 1982. While such webs are generally at parity with fibrous or cloth structures in terms of visual and tactile acceptance by consumers, it is an object of the present invention to provide both "planar" polymeric webs and "macroscopically expanded" polymeric webs exhibiting a visual and tactile impression which is generally consumer prefererd when contrasted to woven and non-woven fibrous webs of comparable macroscopic profile.

It is another object of the present invention to provide webs of the aforementioned type which exhibit fluid-handling and breatheability characteristics not obtainable with woven or non-woven fibrous webs, nor even with prior art polymeric webs.

It is another object of the present invention to provide disposable absorbent bandage structures which employ either "planar" or "macroscopically expanded" plastic webs of the present invention with a high level of consumer preferance over similar absorbent bandage structures employing either woven or non-woven fibrous webs or non-microapertured polymeric webs of the prior art.

DISCLOSURE OF THE INVENTION

The present invention pertains, in a particularly preferred embodiment, to the provision of a microapertured polymeric web exhibiting a fine scale pattern of discrete surface aberrations, each of sid surface aberrations having its amplitude oriented substantially perpendicular to the surface in which the surface aberrations originates. However, unlike prior art webs such as those disclosed in the aforementioned patent to Ahr et al, at least one tiny aperture, i.e., a microaperture, is provided substantially coincidental with the maximum amplitude of each surface aberration. The discontinuity created by the aperture at the peak of each surface aberration substantially reduces its resistance to compression and shear and significantly alters the tactile response of the web.

Although the pattern of microapertured surface aberrations of the present invention, taken as a whole may be visible to the normal naked eye at a perpendicular distance of about 12 inches, the microapertured surface aberrations comprising the pattern are not individually discernible to the normal naked eye when the perpendicular distance between the viewer's eye and the plane of the web is at least about 12 inches. In this regard, the individual microapertured surface aberrations of the present invention preferably have a maximum cross-sectional dimension of about 20 mils or less, most preferably about 10 mils or less, to satisfy the foregoing individual discernibility criteria. The density of fine scale microapertured surface aberrations of the present invention is preferably at least about 3600 aberrations per square inch, as measured in an area which contains the aforementioned treatment, i.e., it is not a requirement that the entire surface of the web be microapertured nor that the web be "planar". Furthermore, the distance between any given microapertured surface aberration and an adjacent aberration in any given direction should not exceed about 25 mils, center-to-center.

While it is not a requirement of the present invention that the microapertured surface aberrations be of the same size or that they form a regulated pattern, in a particularly preferred embodiment, microapertured webs of the present invention may be produced by impinging a jet of high pressure liquid on the exposed surface of a web of flat polymeric film while said film is supported on a fine mesh woven wire support member. The high pressure fluid jet not only causes the smooth flat film to assume the overall knuckle pattern of the woven wire support member, but, in addition, causes fine scale aperturing, i.e., microaperturing, of those portions of the web coinciding with the interstices between the intersecting woven wire filaments comprising the support member. When the microapertured web is removed from the woven wire support member, the surface aberrations corresponding to the interstices between the intersecting wire filaments each exhibit at least one tiny aperture, i.e., a microaperture, substantially coincidental with their point of maximum amplitude.

When using filaments having a diameter of about 7 mils, woven wire support structures having a mesh count of at least about 60 filaments per lineal inch by about 60 filaments per lineal inch, most preferably at least about 80 filaments per lineal inch by a bout 80 filaments per lineal inch, have been found to produce "planar" webs exhibiting a fine scale pattern of microapertured surface aberrations of the present invention.

Quite unexpectedly, it has been found that there is a striking improvement in tactile response exhibited by the surface of the web exhibiting the microapertures (the surface which contacted the woven wire support member during the forming process) when the microapertured web is compared to an otherwise identical web containing similar, but unapertured, surface aberrations. The microapertured web not only apperas substantially non-glossy, but, in addition, exhibits a "soft" and "silky" tactile impression which appears to be preferred by many consumers even over fibrous woven and nonwoven webs of comparable macroscopic profile and pattern.

While not wishing to be bound, it is believed that this marked improvement in tactile impression is a direct result of the microapertures in each of the surface aberrations of the web. In particular, it is believed that unapertured surface aberrations of the type generally taught by the commonly assigned patent to Ahr et al. have a tendency to behave in a manner similar to a supported "arch" when they make contact with the consumer's skin. Introducing a tiny aperture at the peak of the "arch" in each surface aberration of webs of the present invention is believed to greatly reduce the structural resistance of the surface aberration to collapse when compressive and shear forces are applied to its uppermost surface. Accordingly, webs of the present invention exhibit a tactually softer impression due to the presence of the microapertures. In addition, forming a microaperture at the peak of each surface aberration provides in a volcano-like cusp at its peak. The petal shaped edges of the cusp are typically thinned just prior to rupture by the high pressure liquid jet, and are somewhat irregular about the perimeter of the cusp. Accordingly, it is believed that the resultant web surface which is in contact with the human skin is of smaller total area and is less resistant to compressive and shear forces than the unapertured "arch-like" structures taught by Ahr et al. Hence it causes less deflection of the papillary ridges of the skin under an applied force. It is believed that these two factors provide the sudden and unexpected improvement in tactile response, particularly when the skin is used to laterally stroke the surface of the web.

Soft and silky feeling microapertured webs of the present invention can, if desired, be "macroscopically expanded" from their "planar" configuration to provide particularly desirable fluid handling and/or breatheability characteristics, while preserving their markedly improved tactile impression and non-glossy apperance.

Preferred methods and apparatus for forming both "planar" and "macroscopically expanded" webs of the present invention are also disclosed.

BRIEF DESCRIPTION OF THE DRAWINGS

While the specification concludes with claims particularly pointing out and distinctly claiming the present invention, it is believed the present invention will be better understood from the following description in which:

FIG. 5 is a greatly enlarged simplified schematic cross-sectional illustration of a "macroscopically expanded" three-dimensional web formed using a "planar" web of the present invention as a starting material;

DETAILED DESCRIPTION OF THE INVENTION

Figure 1:
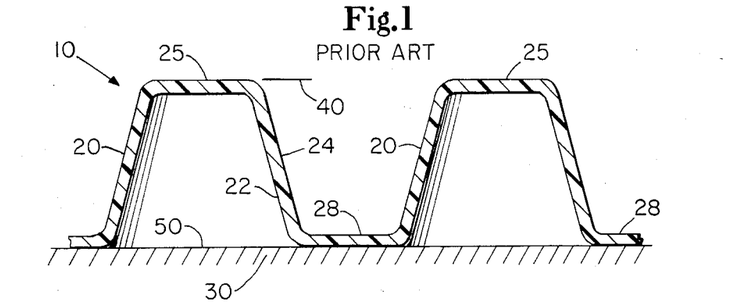
FIG. 1 is a greatly enlarged simplified cross-sectional view of a prior art "planar" polymeric web exhibiting a fine scale pattern of unapertured surface aberrations of the type generally disclosed in the aforementioned commonly assigned patent of Ahr et al.

FIG. 1 is a greatly enlarged simplified cross-sectional view of a segment of a "planar" polymeric web 10 exhibiting a fine-scale pattern of surface aberrations 20 of the type generally disclosed in the aforementioned commonly assigned U.S. Pat. No. 4,463,045 to Ahr et al. which is hereby incorporated herein by reference. The web 10 is shown at rest on a substrate 30 which may be, for example, the absorbent element of a disposable absorbent bandage. The overall caliper of the surface aberrations 20, i.e., the distance separating uppermost plane 40 and lowermost plane 50 is preferably at least about 0.2 mils (i.e., 0.0002 inches), and most preferably at least about 0.3 mils (i.e., 0.0003 inches), generally in accordance with the teachings of the aforementioned patent to Ahr et al. The regularly spaced fine scale pattern of surface aberrations 20 is sufficiently small that the pattern is not discernible to the naked eye when the perpendicular distance between the viewer's eye and the plane of the web is about 12 inches or greater. Furthermore, each of the surface aberrations 20 is free of any planar areas which are large enough to inscribe a 4 mil (i.e., 0.004 inch) diameter circle and is so spaced relative to all of the adjacent surface aberrations that the maximum diameter of any circle which can be inscribed on any planar surface intermediate said surface aberration and any adjacent surface aberration is less than about 4 mils (i.e., 0.004 inches).

According to Ahr et al, the fine scale pattern of surface aberrations 20 is effective in substantially eliminating specular reflection of incident light. The surface aberrations 20 may, if desired, correspond to the interstices between intersecting filaments of a woven wire support member on which the web is subjected to suction while in a heated condition. The valleys 28 intermediate adjacent surface aberrations 20 follow the contour of the filaments which support the web 10 while it is subjected to suction at an elevated temperature. Because the interstices between intersecting filaments in the woven wire support member are physically very tiny, the web 10 is caused to conform to the surface profile of the woven wire support member when subjected to vacuum, but is not apertured at the unsupported interstices. Accordingly the surface aberrations 20 exhibit a closed end wall 25 which is secured about its periphery to the sidewalls of the surface aberration.

As pointed out earlier herein. Web 10 is considered to be a "planar' web, since it exhibits a fine scale pattern of surface aberrations, said pattern not being readily visible to the naked eye when the perpendicular distance between the viewer's eye and the plane of the web is about 12 inches or greater. Although both uppermost surface 24 and lowermost surface 22 of web 10 follow the contour of the woven wire forming structure on which they were supported when subjected to vacuum, the overall caliper of web 10, i.e., the distance between uppermost plane 40 and lowermost plane 50, as shown in FIG. 1, is generally quite small. As is pointed out in commonly assigned U.S. Pat. No. 4,463,045 to Ahr et al., it is preferable that the surface aberrations 20 exhibit an average amplitude of at least about 0.2 mils (i.e., 0.0002 inches), and most preferably at least about 0.3 mils (i.e., 0.0003 inches). According to the teachings of Ahr et al., which are directed to macroscopically expanded three-dimensional webs, improved tactile impression results whenever the surface of the web is divided into at least two distinct planes separated from one another by a distance of at least 0.2 mils (i.e., 0.0002 inches). Because the division is carried out in a fine scale pattern, Ahr suggests that only the reduced area of contact with the uppermost surface of the web is tactually perceived when contacted by human skin.

Figure 2:
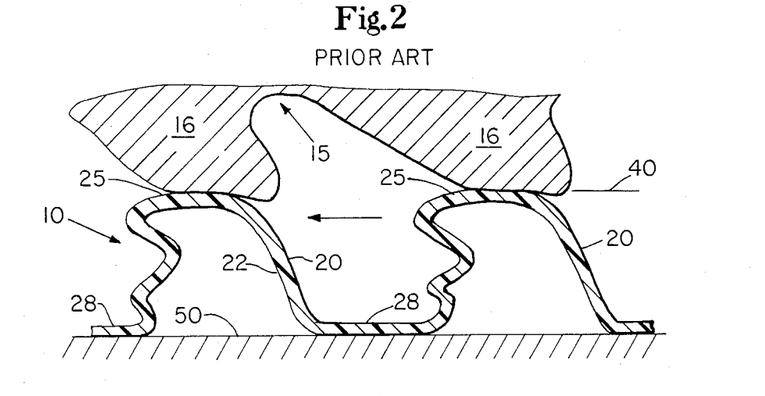
FIG. 2 is a view generally similar to that of FIG. 1 illustrating the response of the surface aberrations and the papillary ridges of the skin on the user's finger to a lateral stroking action applied to the surface of the web via the observer's finger.

FIG. 2 is a view of the web generally shown in FIG. 1 when subjected to a stroking action oriented generally parallel to the surface of the web by the papillary ridges 16 on the skin of the observer's finger 15. As can be seen in FIG. 2, lateral stroking of the web's uppermost surface 24 by a portion of the papillary ridges 16 on the skin of the observer's finger 15 causes the individual surface aberrations 20 to lean generally in the direction of travel of the contacting portion of the observer's finger 15, while the papillary ridges 16 on the observer's skin are deflected in a direction opposite the direction of travel. Note, however, that the closed end wall 25 of each surface aberration tends to keep the side walls of each surface aberrations to which it is secured about its periphery behaving as a discrete structural unit. It is believed that this behavior is much like that of an "arch" to which the side walls of a building are secured, i.e., the presence of the integral end wall 25 structurally reinforces the continuous side wall of each discrete surface aberration, thereby enhancing its resistance both to collapse and shear. Accordingly, it increases the deflection of the papillary ridges 16 of the skin on the observer's finger 15. Although under relatively light pressures the papillary ridges 16 on the skin of the observer's finger 15 contact only a limited portion of each surface aberration 20 as it moves laterally across the surface of the web, it is believed that the aforementioned reinforcing effect of the end walls 25 of each surface aberration tends to impart a resistance to deflection and collapse which detracts from the softness impression experienced by the user's skin. This resistance causes significant deflection of the papillary ridges 16 of the observer's skin which in turn enhances the tactile pattern discernibility as the observer's finger 15 moves laterally across the web's surface.

Figure 3:
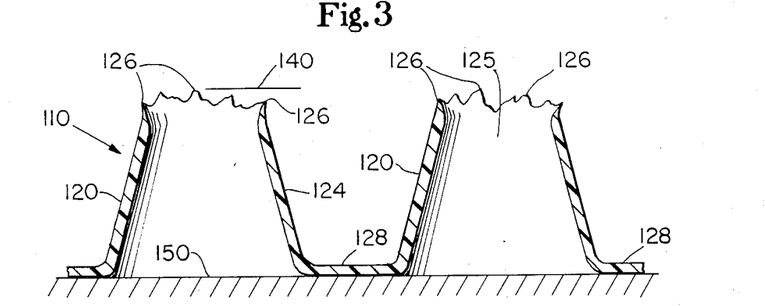
FIG. 3 is a greatly enlarged simplified schematic cross-sectional illustration of a "planar" polymeric web of the present invention illustrating an overall fine scale pattern of surface abberations generally similar to that of the web shown in FIGS. 1 and 2, but depicting the presence of a microaperture at the peak of each surface aberration.

FIG. 3 is a greatly enlarged simplified cross-sectional illustration of a microapertured web 110 of the present invention. The microapertured web 110 exhibits a pattern generally similar to that of prior art "planar" web 10. It may, if desired, be formed on a woven wire support member identical to that employed during formation of prior art "planar' web 10. However, rather than relying upon suction to fully conform the web to the surface of the woven wire support member, a high pressure liquid jet is preferably utilized for this purpose (the details of which will be hereinafter set forth). Because the greater driving force applied by the liquid jet, those portions of the web which coincide with the interstices formed by the intersecting filaments in the woven wire support member are ruptured to form tiny apertures, i.e., microaperture 125 at points which coincide substantially with the maximum amplitude of each surface aberration 120. As can be seen in FIG. 3, rupturing of the surface aberrations 120 at these points results in the formation of a volcano-shaped aperture 125 having relatively thin, irregularly shaped petals 126 about its periphery. As can also be observed from FIG. 3, the outermost extremities of the petals 126 are substantially thin end due to the elongation which occurs just prior to rupture of the film by the high pressure liquid jet. As will be appreciated from an examination of FIG. 3, the overall caliper, i.e. the distance between uppermost plane 140 and lowermost plane 150 of "planar" web 110 is slightly greater than the overall caliper of prior art "planar" web 10 shown in FIG. 1 due to the drawing and thinning which takes place in the end wall of each surface aberration immediately prior to rupture.

The actual size of microaperture 125 is of less importance than its mere existence. The primary benefit of the microaperture on the surface aberration is that it reduces the overall resistance to compression and shear of the surface aberration and destroys its ability to respond as an integral reinforced unit.

Figure 4:
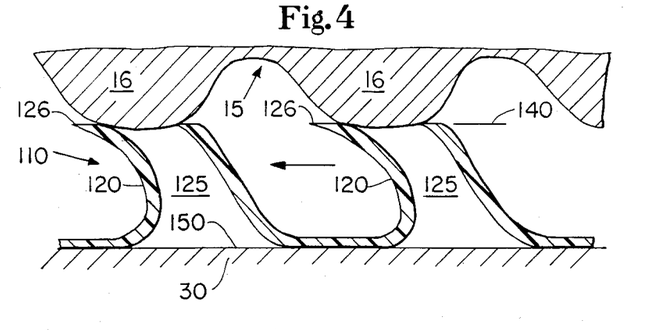
FIG. 4 is a schematic illustration generally similar to that of FIG. 1, but depicting the response of the web of FIG. 3 and the papillary ridges of the skin on the wearer's finger to lateral movement between the observer's finger and the uppermost surface of the polymeric web.

FIG. 4 is a greatly enlarged simplified illustration generally similar to that of FIG. 2, but showing the response of microapertured web 110 of the present invention and the papillary ridges on the skin of the observer's finger when the observer's finger 15 is moved laterally across the surface of the microapertured surface aberrations 120. In particular, note that the overall degree of collapse, i.e., the physical distance between uppermost plane 140 and lowermost plane 150, although initally somewhat greater than that of the prior art unapertured "planar" web shown in FIG. 1, has been reduced to a level less than shown in FIG. 2 for a comparable loading. This is believed due to the elimination of the integral end walls in surface aberrations 120. Because of the existence of microapertures 125 at the center of each of the surface aberrations 120, the overall resistance to collapse of each individual surface aberration 120 is greatly reduced. Furthermore, because of the irregular nature of the petals 126 formed about the periphery of microapertures 125, and the pliable nature of the thinned petals 126, the papillary ridges 15 of the observer's skin are not deflected as much as in FIG. 2. It is believed that all of the foregoing factors contribute to the percpetion that the tactile response of microapertured polymeric "planar" web 110 is substantially softer and silkier than that of prior art web 10.

Figure 5:
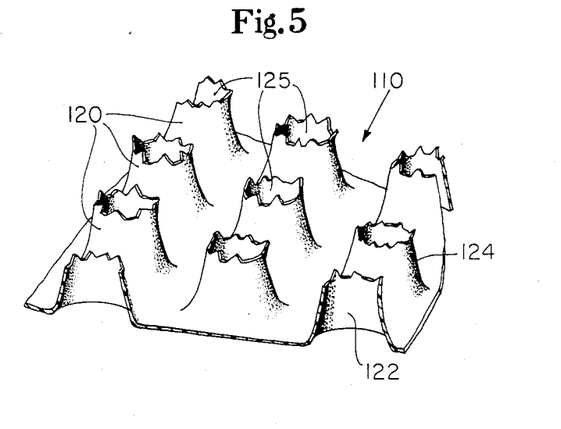
FIG. 5 is a greatly enlarged simplified perspective illustration of a segment of a microapertured "planar" web of the type generally illustrated in cross-section in FIG. 3.

FIG. 5 is a greatly enlarged perspective illustration of a segment of a "planar" microapertured web of the present invention, such as web 110 generally illustrated in FIGS. 3 and 4.

While the tactile impression of "planar" polymeric webs exhibiting a fine scale pattern of surface aberrations of the type generally taught by the aforementioned commonly assigned patent to Ahr et al. generally improves as the amplitude of the surface aberrations increases, such "planar" poymeric webs are generally not perceived as significantly better than woven and nonwoven fibrous structures from a tactile standpoint. Accordingly, it has been necessary to employ macroscopic expansion of such "planar" polymeric webs, often involving patterns designed to simulate the appearance of fibrous woven and nonwoven structures in order to achieve a good consumer response.

By applying the microapeturing criteria of the present invention to fine scale surface aberrations of the type generally taught by Ahr et al. it has most unexpectedly been observed that microapertured webs of the present invention are significantly preferred by many consumers over fibrous woven and nonwoven structures. It is believed that it is the introduction of at least one microaperture substantially coincident with the point of maximum amplitude on each surface aberration which gives rise to the shift in consumer preferance generally toward microapertured polymeric webs of the present invention over fibrous woven and nonwoven structures of generally similar macroscopic cross-section and pattern.

Another unexpected result of applying the microapeturing criteria of the present invention to surface aberrations of even larger cross-section than those taught by Ahr et al. is that consumer preference remains with webs of the present invention even when the pattern of surface aberrations becomes discernible by the normal naked eye at a perpendicular distance of about 12 inches.

Figure 6:
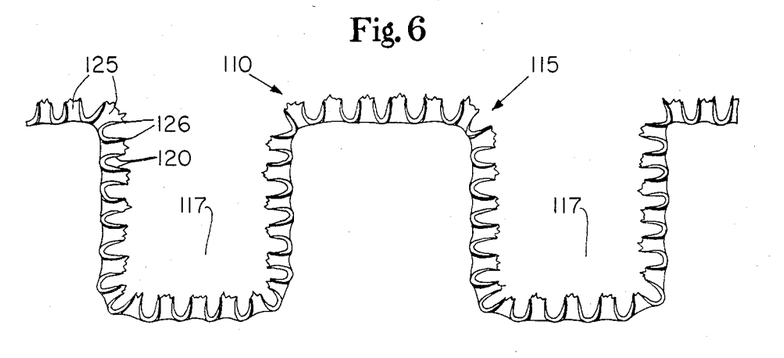

It is of course recognized that microapertured "planar" webs 110 of the present invention may, if desired, be "macroscopically expanded" to form a three-dimensional polymeric web. Exemplary of macroscopically expanded webs are those generally taught by the aforementioned commonly assigned U.S. Pat. No. 4,342,314 to Radel et al., said patent being hereby incorporated herein by reference. Macroscopic expansion is preferably carried out by orienting the microapertured surface aberrations 120 so that microapertures 125 form the skin contacting surface of the macroscopically expanded web 115, as generally shown in FIG. 6. The resilience imparted by macroscopic expansion of the web is superposed on that exhibited by the microapertured surface aberrations 120 of "planar" web 110.

Macroscopic debossments 117 in web 115 may be of any particular shape and size desired by creating a forming structure as generally taught by commonly assigned U.S. Pat. No. 4,395,215 issued to Bishop on July 26, 1983 and hereby incorporated herein by reference. The teachings of the Bishop patent are particularly useful in the event macroscopic expansion without macroscopic aperturing of the web is desired. In such case, it is necessary to provide at least one of the lamina in the three-dimensional forming structure with a very fine pattern of apertures sufficient to support the bottom of the macroscopic debossments 117 without permitting macroscopic rupturing thereof during the macroscopic expansion process.

Figure 7:
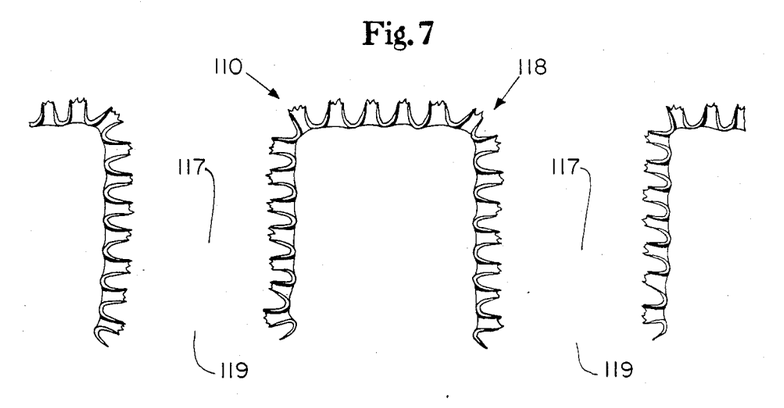
FIG. 7 is a view generally similar to that of FIG. 6, but showing an alternative embodiment of a "macroscopically expanded", macroscopically apertured three-dimensional polymeric web formed using a "planar" web of the present invention as a starting material.

An alternative macroscopically expanded web 118 of the present invention is illustrated in greatly enlarged form in FIG. 7. The web shown in FIG. 7 is generally similar to that shown in FIG. 6, with the exception that the end walls of the debossments 117 have been ruptured to form macroscopic apertures 119. This may be accomplished by using a forming structure of the type disclosed in the aforementioned commonly assigned U.S. Pat. No. 4,342,314 to Radel et al., which is incorporated herein by reference.

Figures 8, 8A, 8C:
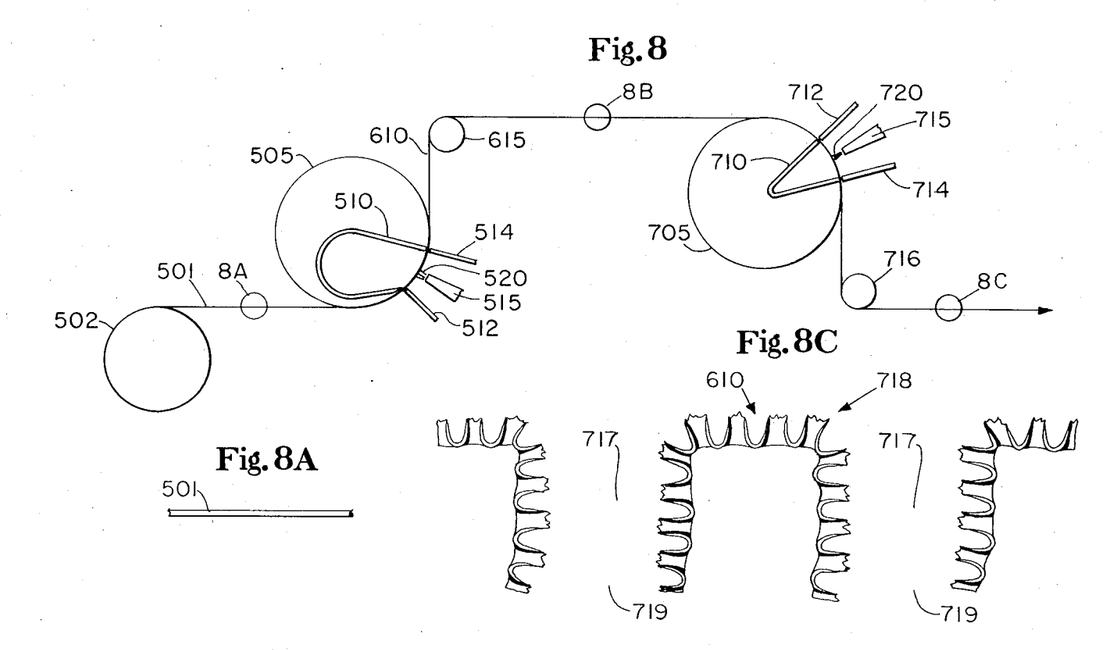
FIG. 8 is a greatly simplified schematic illustration of a preferred process for forming a "planar" microapertured web of the present invention and thereafter "macroscopically expanding" said planar web to a three-dimensionsl configuration which may, if desired, also be marcoscopically apertured.
FIG. 8A is a greatly enlarged inset of the web shown in FIG. 8 prior to any processing.
FIG. 8C is a greatly enlarged inset of the microapertured web shown in FIG. 8 after it has been "macroscopically expanded" and macroscopically apertured.

FIG. 8 is a simplified schematic illustration of a particularly preferred process for forming a "planar" polymeric web containing a pattern of microapertured surface aberrations of the present invention and for further processing said "planar" microapertured polymeric web to form a "macroscopically expanded" and if desired, a macroscopically apertured three-dimensional web generally similar to that shown in FIG. 7.

Figure 8B:
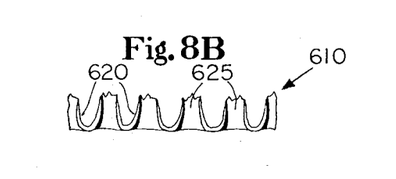
FIG. 8B is a greatly enlarged inset of the microapertured web shown in FIG. 8 while it is still in a "planar" condition.

In particular, a web of substantially smooth flat polymeric material 501 is fed from a supply roll 502 onto the surface of a woven wire support member 505 which rotates about a stationary vacuum chamber 510. The cross-section of the incoming web 501 is shown in greatly enlarged form in the inset of FIG. 8A. A high pressure liquid jet nozzle 515 is directed at the exposed surface of the substantialy smooth flat film 501 intermediate a pair of baffles 512, 514 as the web traverses the vacuum chamber. The high pressure, i.e., preferably at least about 800 psig, jet of liquid 520 causes the smooth flat web 501 to assume the general contour of the knuckle pattern of the woven wire support member 505. In addition, because the interstices formed by the intersecting filaments are unsupported, the fluid jet causes rupture at those portions of web 501 coinciding with the interstices in the woven wire support structure 505, thereby producing a "planar" microapertured web 610, a segment of which is shown in greatly enlarged form in the inset of FIG. 8B. "Planar" microapertured web 610 exhibits a multiplicity of fine scale surface aberrations 620 generally similar to aberrations 120 of web 110. The microapertures 625 coincide with the point of maximum amplitude of the surface aberrations 620. (It is, of course, recognized that more complex weaving patterns can be utilized to produce more than a single microaperture in any given surface aberration without deviating from the scope of the present invention.) Thus web 610 is substantially identical to web 110 shown generally in FIG. 3 an 4.

"Planar" microapertured web 610 is removed from the surface of woven wire forming structure 505 and passed about idler roll 615.

If the web 610 is to be macroscopically expanded, it is thereafter forwarded with surface aberrations 620 generally outwardly oriented about the periphery of a macroscopic patterned three-dimensional forming structure 705 which rotates about a second stationary vacuum chamber 710. A second high pressure liquid nozzle 715 is located intermediate stationary baffles 712, 714. High pressure liquid nozzle 715 applies a high pressure, i.e., preferably at least about 400 psig, liquid jet 720 substantially across the entire width of "planar" microapertured web 610. The high pressure liquid jet 720 causes macroscopic expansion of the "planar" web 610 to a three-dimensional configuration generally resembling that of the forming structure 705 prior to removal about idler roll 716. If the forming structure exhibits macroscopic cross-section apertures, the high pressure liquid jet will also rupture the end walls of the capillary networks formed in the web.

A greatly enlarged segment of the resulting macroscopically expanded and macroscopically apertured web 718 is shown in the inset of FIG. 8C. The macroscopically expanded web 718 exhibits a multiplicity of debossments 717 each having a macroscopic aperture 719 located at its lowermost end. As with the web embodiment 118 illustrated generally in FIG. 7, the microapertured surface aberrations 610 are outwardly oriented during the macroscopic expansion process so that the skin contacting surface of the macroscopically expanded web 718 comprises the edges of the microapertures 625 formed in each of the surface aberrations 620.

More specific details as to the nature of the process generally described in relation to FIG. 8 are disclosed in connection with FIG. 1 of the commonly assigned U.S. Patent Application of John J. Curro, James C. Baird, Donald L. Gerth, George M. Vernon and E. Kelly Linman, entitled Multi-phase Process for Debossing and Perforating a Polymeric Web to Coincide with the Image of One or More Three-Dimensional Forming Structures, U.S. Pat. No. 4,609,518, filed concurrently herewith and hereby incorporated herein by reference.

While particular embodiments of the present invention have been illustrated and described, it will be obvious to those skilled in the art that various changes and modifications can be made without departing from the spirit and scope of the invention. Whether in a "planar" configuration or a "macroscopically expanded" three-dimensional configuration, polymeric webs exhibiting microapertured surface aberrations of the present invention exhibit a highly preferred visual and tactile impression when compared to fibrous woven and nonwoven webs of similar macroscopic cross-section and pattern. In addition, such microapertured polymeric webs of the present invention are generally much more quiet than non-apertured polymeric webs of the prior art, i.e., they do not tend to make rustling noises when they undergo movement. This factor is particularly important when the webs are used as topsheets and/or backsheets in a garment such as disposable adult incontinent brief, since rustling sounds made by the brief when the wearer's body undergoes movement can cause embarrassment to the wearer.

While the present invention has been described primarily in the context of either a wearer contacting topsheet or a backsheet for a disposable absorbent bandage such as a disposable diaper, an incontinent brief or the like, webs of the present invention may find many other applications in other environments, such as in the field of wearing apparel. It is intended to cover in the appended claims all such modifications and applications that are within the scope of this invention.

What is claimed is:

1. A microapertured polymeric web exhibiting a soft and silky tactile impression on at least one surface thereof, said silky feeling surface of said web exhibiting a pattern of discrete volcano-like surface aberrations which are not individually discernible to the normal naked eye when the perpendicular distance between said web and the observer's eye is at least about 12 inches, the density of said surface aberrations being at least about 3,600 per square inch, the center-to-center distance between adjacent surface aberrations not exceeding about 25 mils, each of said surface aberrations having its amplitude oriented substantially perpendicular to the surface in which said surface aberration originates and exhibiting a maximum cross-sectional dimension not exceeding about 20 mils, as measured perpendicular to its amplitude, the end of each of said surface aberrations further including at least one microaperture substantially coincidental with its point of maximum amplitude, said microaperture exhibiting a multiplicty of thin, irregularly shaped petals about its periphery, said microaperture further creating a discontinuity which reduces the resistance to compression and shear of each of said surface aberrations as well as the degree of contact with the observer's skin, whereby the tactile impression of said web is pereived as generally soft and silky.

2. The web of claim 1, wherein said pattern of microapertured surface aberrations comprises a regularly repeating pattern.

3. The web of claim 2, wherein said microapertured surface aberrations correspond to the interstices formed between the intersecting filaments of a woven wire mesh support structure on which said web is supported during processing and from which said web is thereafter separated.

4. The web of claim 3, wherein said woven wire mesh support structure exhibits a mesh count of at least about 60 filaments per lineal inch by about 60 filaments per lineal inch.

5. The web of claim 3, wherein said woven wire mesh support structure exhibits a mesh count of at least about 80 filaments per lineal inch by about 80 filaments per lineal inch.

6. The web of claim 1, wherein there are substantially no planar areas large enough to inscribe a 4 mil diameter circle on the surface of said web exhibiting said microapertured surface aberrations.

7. The web of claim 1, said web further exhibiting a macroscopically expanded, three-dimensional pattern of macroscopic cross-section surface aberrations superposed thereon, said macroscopic cross-section surface aberrations being oppositely oriented from said microapertured surface aberrations.

8. The web of claim 7, wherein the end of each of said macroscopic cross-section surface aberrations includes a macroscopic cross-section aperture substantially coincidental with the point of maximum amplitude of said macroscopic cross-section surface aberration.

* * * * *

UNITED STATES PATENT AND TRADEMARK OFFICE
CERTIFICATE OF CORRECTION

PATENT NO. : 4,629,643
DATED : December 16, 1986
INVENTOR(S) : JOHN J. CURRO and E. KELLY LINMAN It is certified that error appears in the above-identified patent and that said Letters Patent is hereby corrected as shown below:

Title Page, lines 14-15 of ABSTRACT, "vol-croaperture" should read -- volcano-like edges formed at the periphery of each microaperture --.

Column 1, line 13, "abberations" should read -- aberrations --.

Column 1, line 16, "operature" should read -- aperture --.

Column 4, line 20, "cloth-ike" should read -- cloth-like --.

Column 4, lines 27-28, "percieved" should read -- perceived --.

Column 5, line 12, "preferance" should read -- preference --.

Column 5, line 21, "sid" should read -- said --.

Column 5, line 23, "aberrations" should read -- aberration --.

Column 5, line 25, "al," should read -- al., --.

Column 6, line 12, "a bout" should read -- about --.

Column 6, line 24, "apperas" should read -- appears --.

Column 6, line 65, "apperance" should read -- appearance --.

Column 7, line 21, "abberations" should read -- aberrations --.

Column 7, line 26, "1," should read -- 2, --.

UNITED STATES PATENT AND TRADEMARK OFFICE
CERTIFICATE OF CORRECTION

PATENT NO.   :   4,629,643

DATED        :   December 16, 1986

INVENTOR(S)  :   JOHN J. CURRO and E. KELLY LINMAN

It is certified that error appears in the above-identified patent and that said Letters Patent is hereby corrected as shown below:

Column 7, line 34, "5" should read -- 6 --.

Column 7, line 47, "dimensionsl" should read -- dimensional --.

Column 8, line 37, ". Web" should read -- , web --.

Column 9, line 8, "aberrations" should read -- aberration --.

Column 9, line 54, "thin end" should read -- thinned --.

Column 10, line 10, "initally" should read -- initially --.

Column 10, line 24, "percpetion" should read -- perception --.

Column 10, line 54, "preferance" should read -- preference --.

Column 11, line 53, "substantialy" should read -- substantially --.

Column 12, line 7, "an" should read -- and --.

Column 14, line 2, Claim 1, "pereived" should read -- perceived --.

Signed and Sealed this

Thirty-first Day of March, 1987

*Attest:*

DONALD J. QUIGG

*Attesting Officer*     *Commissioner of Patents and Trademarks*